United States Patent [19]

Schumann

[11] Patent Number: Plant 5,980

[45] Date of Patent: May 12, 1987

[54] GERANIUM PLANT NAMED GEMINI

[75] Inventor: Ingeborg Schumann, Bad Ems, Fed. Rep. of Germany

[73] Assignee: Fischer Geraniums, Inc., Curacao, Netherlands Antilles

[21] Appl. No.: 761,008

[22] Filed: Jul. 31, 1985

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A geranium plant named Gemini having white to red flower color, startel flower type with strong divided petals; novel; decorative zonal foliage; compact growth habit with good branching; very early response; and heavy flower yield.

2 Drawing Figures

1

The present invention comprises a new and distinct cultivar of geranium, botanically known as *Pelargonium zonale,* and hereinafter referred to by the cultivar name Gemini.

Gemini is a product of a planned breeding program which had the objective of creating new geranium cultivars having novel startel flower type and unique leaf shape.

Gemini was originated from a hybridization made by Ingeborg Schumann in a controlled breeding program in Hillscheid, Federal Republic of Germany in 1978. The female parent was an inbred line from H42 and Stellar Artic Star. The male parent of Gemini was Stellar Orange. Both parents are unpatented.

Gemini was discovered and selected as one flowering plant within the progeny of the stated cross by Ingeborg Schumann on July 7, 1979 in a controlled environment in Hillscheid, Federal Republic of Germany.

The first act of asexual reproduction of Gemini was accomplished when vegetative cuttings were taken from the initial selection in January of 1980 in a controlled environment in Hillscheid, Federal Republic of Germany by a technician working under formulations established and supervised by Ingeborg Schumann. Horticultural examination of selected units initiated in the spring of 1980 and continuing in 1981 through 1983 has demonstrated that the combination of characteristics as herein disclosed for Gemini are firmly fixed and are retained through successive generations of asexual reproduction.

Gemini has not been observed under all possible environmental conditions. The phenotype may vary significantly with variations in environment such as temperature, light intensity, and day length. The following observations, measurements and comparisons describe plants grown in Hillscheid, Federal Republic of Germany, under conditions which approximate those generally used in commercial practice.

The following traits have been repeatedly observed and are determined to be basic characteristics of Gemini, which in combination distinguish this geranium as a new and distinct cultivar.

1. Red and light pink to white flowers having star shaped petals; divided petals are strong.
2. Novel leaf shape; very decorative.
3. Compact habit with good branching.
4. Very early flowering.
5. Heavy flower yield in spring and summer.

2

The accompanying photographic drawings shows typical flower and foliage characteristics of Gemini, with colors being as true as possible with illustrations of this type. Sheet 1 is a color photograph showing Gemini in perspective view. Sheet 2 is a black and white print showing the novel leaf shape of Gemini, at three stages of growth.

In the following description color references are made to The Royal Horticultural Society Colour Chart. The color values were determined between 2:00 p.m. and 3:00 p.m. on May 15, 1985 under 20,000 Lux light intensity at Hillscheid, Federal Republic of Germany.

Classification:

*Botanical.*—A hybrid of the genus *Pelargonium l'hert* and species *Pelargonium zonale.*

*Commercial.*—Gemini.

INFLORESCENCE

A. Umbel:

*Average diameter.*—85 mm.

*Average depth.*—49 mm.

*Peduncle length.*—159 mm.

*Pedicel length.*—28 mm.

B. Corolla:

*Average diameter.*—40 mm.

*Form.*—Single flower; petals have relatively sharp tips.

*Color (general tonality from a distance of three meters).*—Red to light pink to white. Upper Petals: Generally white 155C-D with pink to red tips, red color generally 42A. Lower Petals: Red, 42A.

C. Bud:

*Shape.*—Elongated, flat top.

*Color.*—Red to white.

D. Reproductive organs:

*Androecium.*—Mostly sterile; sometimes 5–7 anthers.

*Gynoecium.*—5 lobed stigma.

E. Spring flowering response period: In Hillscheid, Federal Republic of Germany, in 1983, 95% of plants opened with at least one flower 13 weeks after planting of unrooted cuttings.

F. Outdoor flower production: The total flower count in 1983 in Hillscheid, Federal Republic of Germany, was between 65 and 68 flowers per plant for the June through October observation period.

G. Durability: Good.

PLANT

A. Foliage:

*Form.*—Generally cup-shaped.

*Margin.*—Deeply indented, forming marginal leaf segments; leaf tips relatively pointed.

*Color.*—Top Surface: Medium green, approximately 137B-C. Zonation: Generally brown, medium zonation, primarily at margin of leaves.

*Tolerance of botrytis.*—Good.

B. General appearance and form:

*Internode length.*—18 mm.

*Branching pattern.*—4.9 branches within a period of 13 weeks cultivation from unrooted cuttings.

*Height.*—250 mm.

I claim:

1. A new and distinct cultivar of geranium named Gemini, as described and illustrated, and particularly charcterized by its white to red flower color, star shaped and strong divided petals; novel, decorative zonal foliage; compact growth habit with good branching; very early response; and its heavy flower yield.

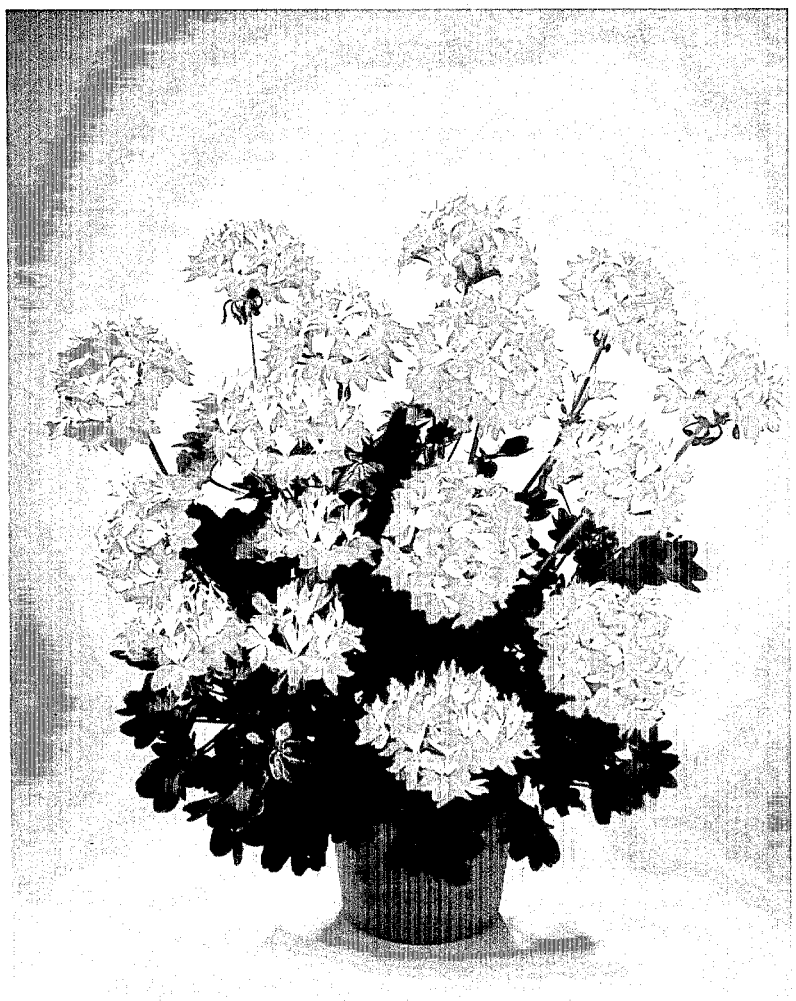

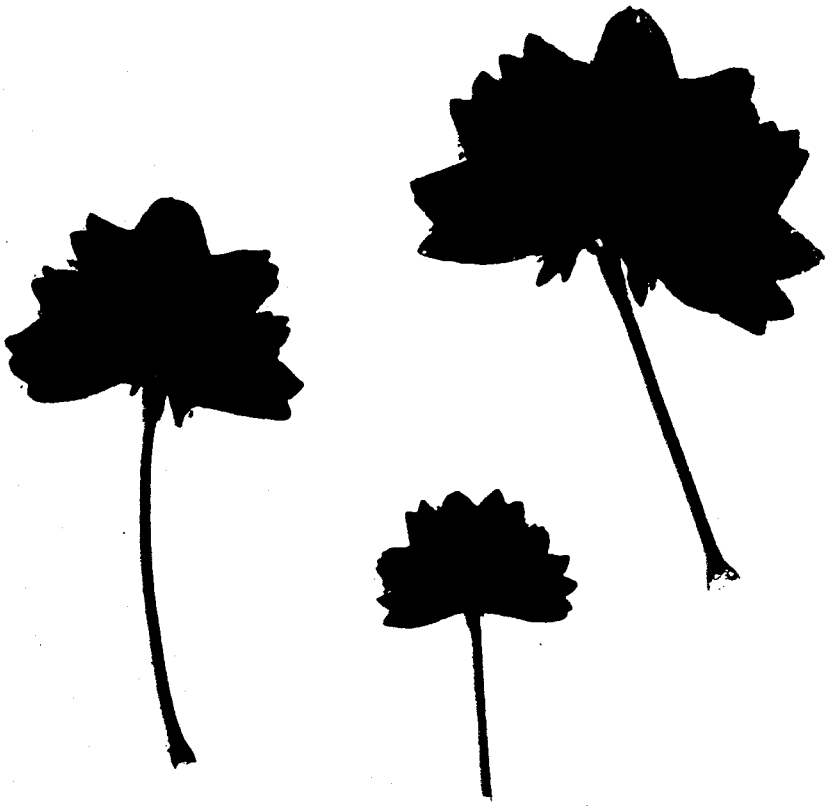

* * * * *